(12) United States Patent
Powell et al.

(10) Patent No.: US 7,854,394 B2
(45) Date of Patent: Dec. 21, 2010

(54) TIMED AEROSOL FRAGRANCE DISPENSER FOR FORCED-AIR DUCT INSTALLATION

(76) Inventors: Michael Mac Powell, 163 E. 1450 North, Lehi, UT (US) 84043; Aaron M. Best, 5431 Avalon Dr., Salt Lake City, UT (US) 84107; David J. Havell, 3275 Gregson Ave., Salt Lake City, UT (US) 84109

( * ) Notice: Subject to any disclaimer, the term of this patent is extended or adjusted under 35 U.S.C. 154(b) by 163 days.

(21) Appl. No.: 12/351,810

(22) Filed: Jan. 9, 2009

(65) Prior Publication Data

US 2009/0127351 A1 May 21, 2009

Related U.S. Application Data

(63) Continuation-in-part of application No. 11/903,763, filed on Sep. 24, 2007, now abandoned.

(60) Provisional application No. 60/846,588, filed on Sep. 23, 2006.

(51) Int. Cl.
*B05B 1/08* (2006.01)
*B05B 17/06* (2006.01)

(52) U.S. Cl. ............... 239/102.2; 239/70; 422/123; 422/124; 454/337

(58) Field of Classification Search ............ 239/4, 239/67–70, 99, 102.1, 102.2, 282, 302, 326; 422/4, 5, 105, 123, 124; 222/14, 52, 57, 222/638, 645, 646, 648, 649; 261/115, 118, 261/119.1, DIG. 88; 454/157, 337, 370
See application file for complete search history.

(56) References Cited

U.S. PATENT DOCUMENTS

| 4,903,583 | A | * | 2/1990 | Frazier | 454/337 |
| 5,924,597 | A | * | 7/1999 | Lynn | 222/1 |
| 6,347,992 | B1 | * | 2/2002 | Durbin et al. | 454/337 |
| 6,379,242 | B1 | * | 4/2002 | Wiseman et al. | 454/337 |
| 6,722,529 | B2 | * | 4/2004 | Ceppaluni et al. | 222/63 |

* cited by examiner

*Primary Examiner*—Darren W Gorman
(74) *Attorney, Agent, or Firm*—Angus C. Fox, III (57) ABSTRACT

A timed aerosol fragrance dispenser includes a housing containing a programmable microprocessor, a low-voltage DC power source, a piezoelectric assembly for spraying timed bursts of fragrance, and circuitry for activating the piezoelectric assembly, and a magnetic reed switch air flow detector. A fragrance-containing reservoir attaches to the housing, which incorporates a clip which allows the dispenser to be secured to a heating and air conditioning vent register. When the air flow detector senses air flow from the vent register, the microcontroller in combination with other circuitry generates current pulses having a voltage sufficiently high to activate the piezoelectric assembly. Intervals between pulses are switch selectable. In addition, the normal programming can be overridden to spray fragrance for a set period even in the absence of air flow from the vent register.

6 Claims, 13 Drawing Sheets

TIMED AEROSOL FRAGRANCE DISPENSER FOR FORCED-AIR DUCT INSTALLATION

This is a continuation-in-part of application Ser. No. 11/903,763, which was filed on Sep. 24, 2007, now abandoned, and which has a priority date based on the filing of provisional patent application No. 60/846,588, titled TIMED AEROSOL FRAGRANCE DISPENSER FOR FORCED-AIR DUCT INSTALLATION, on Sep. 23, 2006.

FIELD OF THE INVENTION

This invention relates, generally, to fragrance dispensers and, more particularly, to fragrance dispensers designed for placement within a heating/air-conditioning duct behind a vent register.

BACKGROUND OF THE INVENTION

The annual market for air freshener products in the U.S. is nearly $3 billion. Plug-in type air freshener products account for a third of that market. Over the past decade, battery-operated, metered aerosol fragrance dispensers have become popular in commercial settings such as public and office restrooms. As these devices are typically somewhat complex, in that they incorporate a DC electric motor, a gear drive operated by the motor which actuates the spray valve, an aerosol fragrance canister, and a programmable timer for adjusting the time interval between sprays, average retail prices of around $50 were too costly to generate widespread demand for home use. However, prices have dropped dramatically. For example, Wal-Mart now sells a programmable Air Wick® dispenser with one aerosol fragrance canister for less than $10. As the cost of a replacement fragrance canister is nearly $4, it appears that American Home Products Corporation may be selling the Air Wick® fragrance dispenser at less than cost, a marketing strategy learned from Gillette's sale of razor blades and Hewlett-Packard's sale of ink cartridges.

One problem associated with the use of fragrance dispensers is that it is difficult to disseminate fragrance throughout an entire home, as air circulation within the home is typically inadequate. In order for fragrance dispersion to be truly effective, a fragrance dispenser would be required in nearly every room of the home. Although many home owners would prefer to have a pleasing fragrance dispersed throughout their homes, the fragrance dispensers, though not necessarily unsightly, can hardly be mistaken for home decor. Although automobiles provide a much more confined environment than do houses, the use of a fragrance dispenser within an automobile suffers from the same problems: dispensers are generally unsightly and fail to disperse the fragrance evenly throughout the interior.

What is needed is an apparatus for dispensing fragrances throughout a home or other structure, such as an automobile interior, that provides generally uniform dispersion of fragrances throughout the entire interior space, while being generally hidden from view.

SUMMARY OF THE INVENTION

The present invention provides multiple embodiments of an apparatus that fulfills the heretofore expressed need for an apparatus which dispenses fragrances in a generally enclosed space, such as the interior of an automobile. The apparatus, which is a timed aerosol dispenser, functions in combination with a forced-air heating and air-conditioning system and is installed either behind or in front of a vent register of the heating and air-conditioning system, or in the furnace/mechanical room or closet of a building such that the aerosol spray is discharged into the primary distribution duct.

A preferred embodiment of the timed aerosol dispenser includes a housing, a fragrance-containing reservoir that is mountable to the housing, and a piezoelectric assembly for spraying timed bursts of fragrance. The housing incorporates a clip which allows the dispenser to be attached to a heating and air conditioning vent register. A single 1.5-volt power cell provides electrical power for the device. Charge from the battery is continually stored in a capacitor. The charge escapes from the capacitor through a transistor which is activated periodically by pulses generated by a programmable microcontroller. Pulse frequency is selectable using a multi-position switch on the front of the device. Pulses are ordinarily generated only when there is air flow emanating from the vent register. A momentary contact switch allows the normal program to be overridden for a set period of time so that the device will emit fragrance for a programmed period even in the absence of air flow from the vent register. After the programmed period expires, the device reverts to normal operation requiring air flow for the dispensing of fragrance. The charge escaping through the transistor is passed through a switching transformer, which increases the voltage to a level sufficient to activate the piezoelectric assembly. Rather than using a costly device, such a mass flow controller or mass flow meter to detect air flow, the timed aerosol dispenser of the present invention detects air flow from the vent register using a magnetic reed switch which incorporates a plastic film flap that activates the reed switch when moved by air flow. Heretofore, magnetic reed switches incorporating plastic film flap actuators were used to detect a failure of a cooling fan in a computer case. The present use of such a switch is considered novel.

PREFERRED EMBODIMENT OF THE INVENTION

The various embodiments of the invention will now be described in detail with reference to the attached drawing figures. It is to be understood that the drawings are not necessarily drawn to scale and that they are intended to be merely illustrative.

Figure 1:
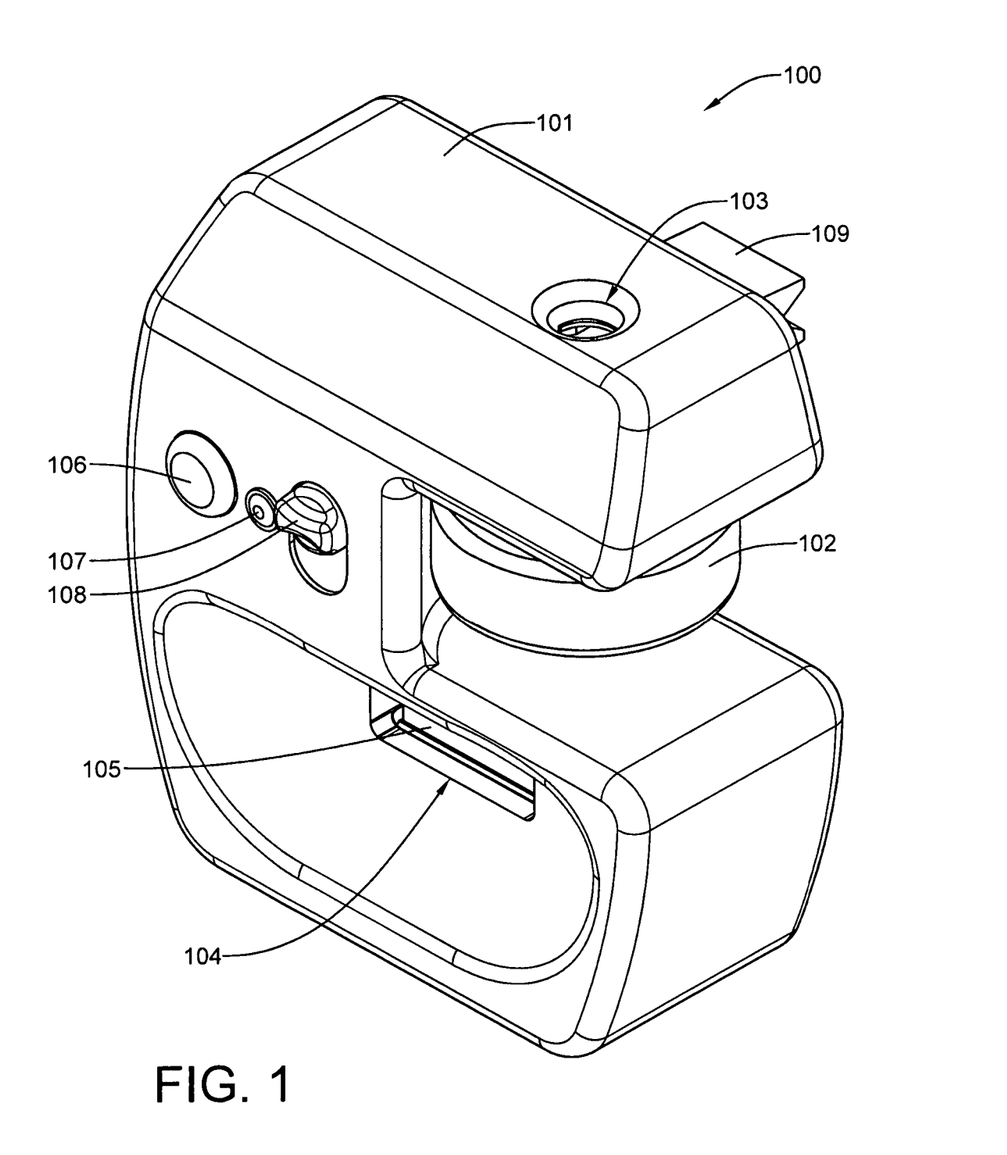
FIG. 1 is an isometric view of the micro fragrance dispenser, showing the front, the top and right side thereof.

Referring now to FIG. 1, the new micro fragrance dispenser 100 has a housing 101 made of a structural thermoplastic polymer material, a reservoir 102 containing fragrance oils that are either undiluted or diluted with non-polar solvents, an aperture 103 in the top of the housing 101 through which small quantities of fragrance oils are periodically sprayed, a front window 104 in the housing 101 in which is installed an air flow sensor 105, a momentary contact switch 106 which turns on the dispenser for a set period of time, an indicator LED 107 that signals operating conditions of the dispenser 100, a three-position slider switch 108 with which the spraying frequency of the dispenser 100 can be set, and a clip 109 which can be used to attach the dispenser 100 to air duct registers. For a presently preferred embodiment of the dispenser, the housing 100 has a height of approximately 67 mm, a width of approximately 60 mm, and a depth (excluding the clip 108) of approximately 25 mm.

Figure 2:
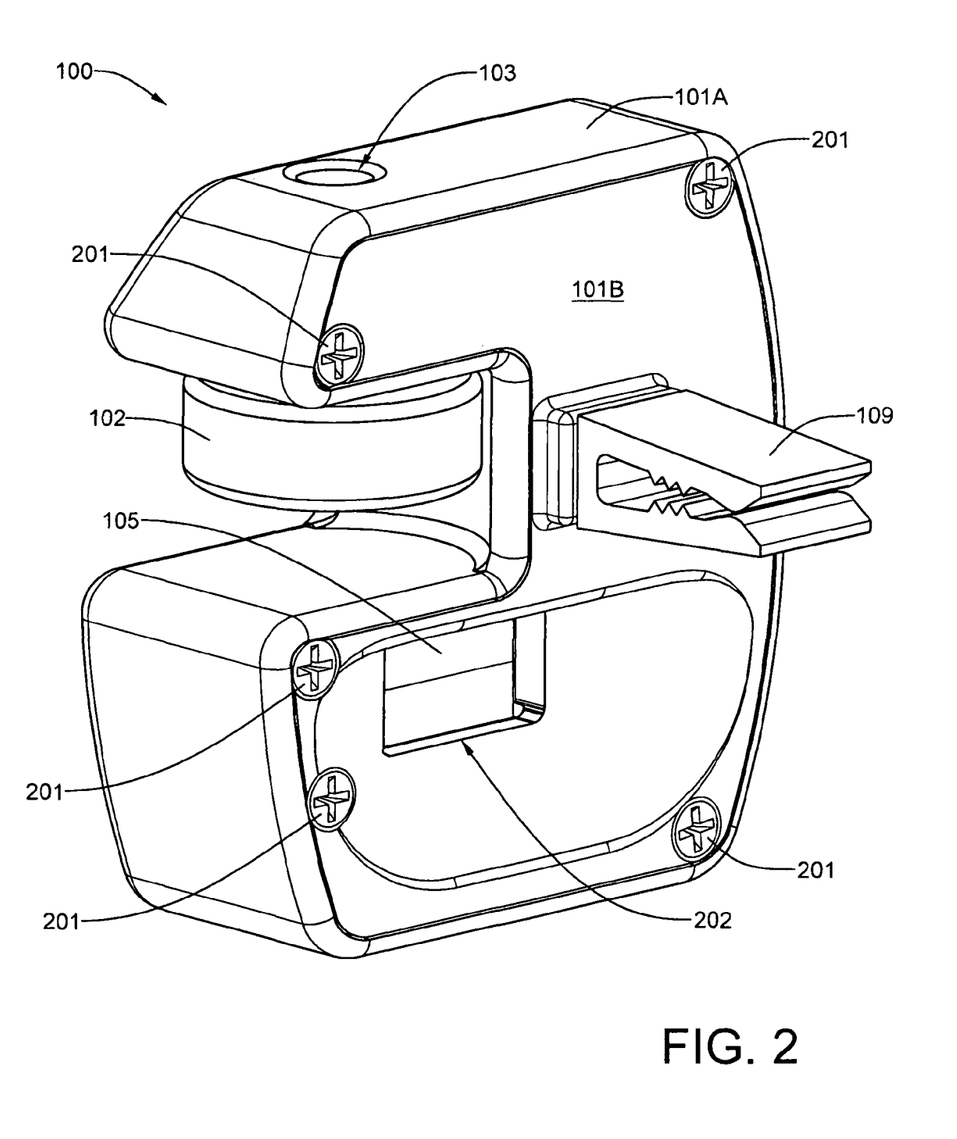
FIG. 2 is an isometric view of the micro fragrance dispenser, showing the rear, the top and the right side thereof.
Figure 3:
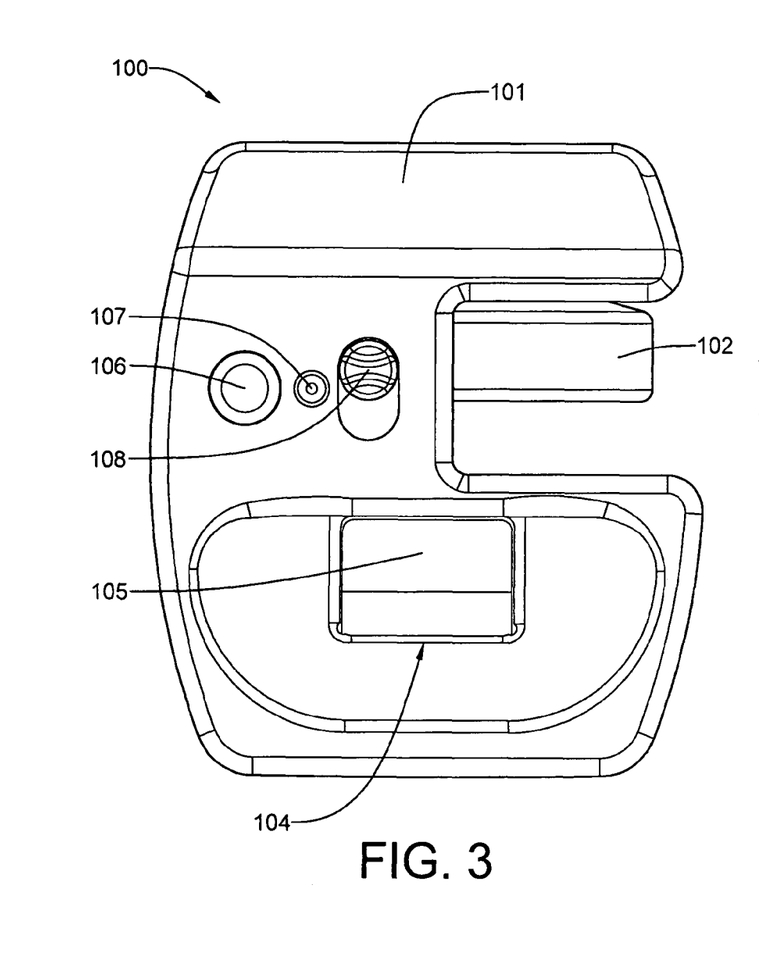
FIG. 3 is a front elevational view of the micro fragrance dispenser.
Figure 4:
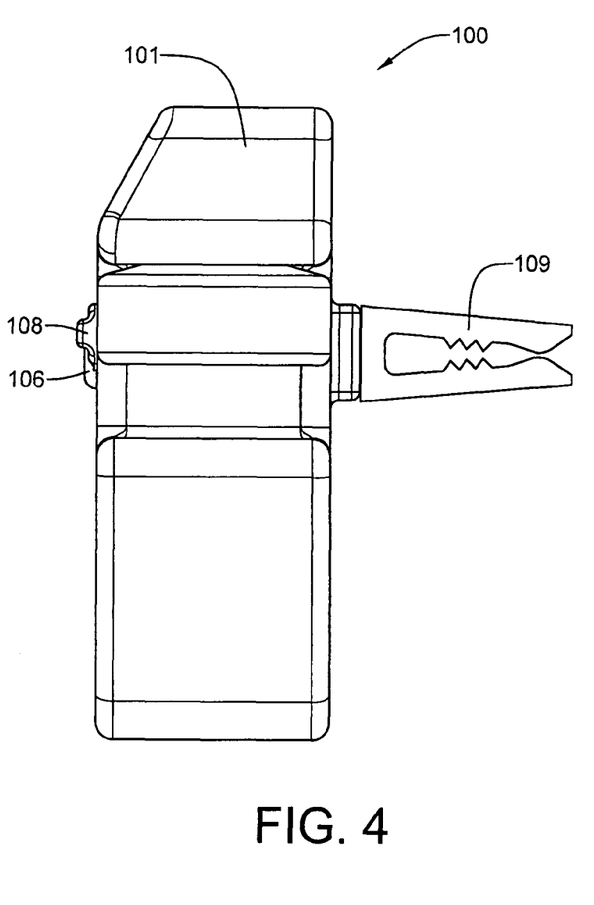
FIG. 4 is a right-side elevational view of the micro fragrance dispenser.
Figure 5:
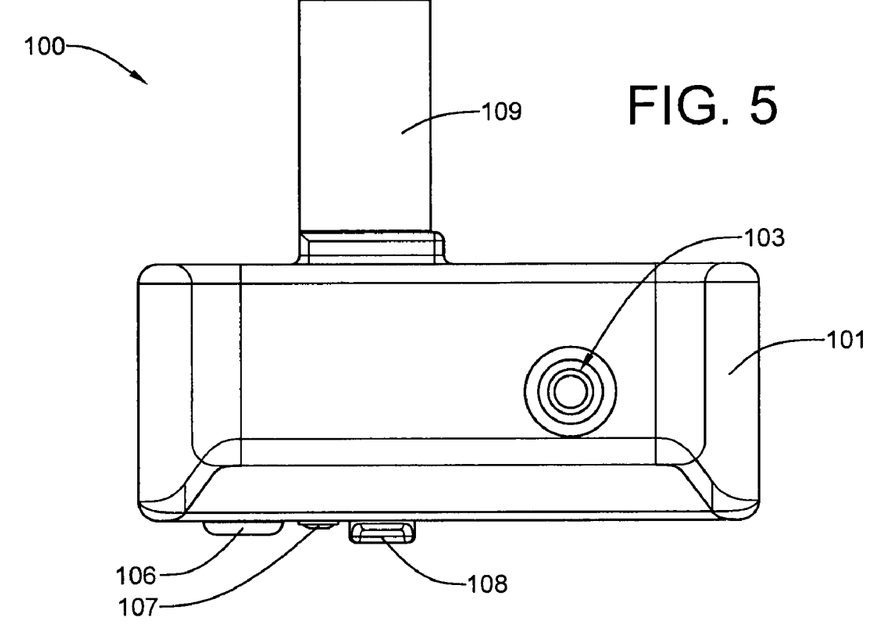
FIG. 5 is a top plan view of the micro fragrance dispenser.
Figure 6:
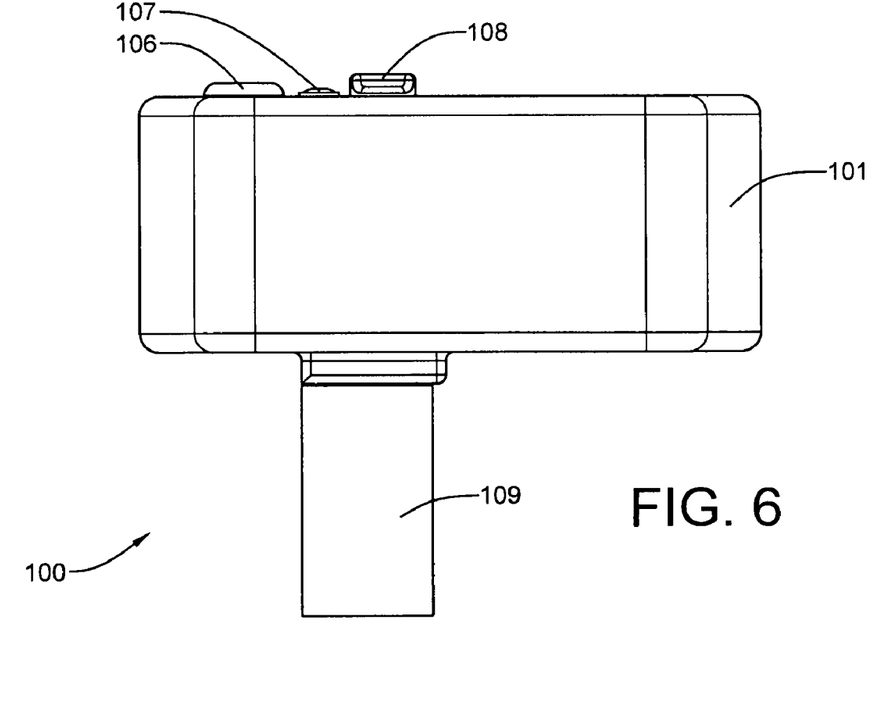
FIG. 6 is a bottom plan view of the micro fragrance dispenser.

Referring now to FIG. 2, the construction of the new micro fragrance dispenser 100, the construction of the housing 101 is evident. The housing 101 consists of a front main portion 101A and a rear panel 101B, which is secured to the front main portion 101A with five self-tapping screws 201. The clip 109, which is secured to the rear panel 101B, is more fully visible in this view. It will be noted that the rear panel 101B has a rear window 202, which aligns with the front window 104 in the front main portion 101A.

The structural thermoplastic polymers from which the housing 101 may be injection molded include polyethylene acrylonitrile butadiene styrene (ABS), polyethylene terephthalate (PET), polybutylene terephthalate (PBT), polycarbonate (PC), polyvinylchloride (PVC), polyamide (PA or nylon), and polypropylene (PP). High-performance thermoplastic resins, such as polyetheretherketone (PEEK), polyetherketone (PEK), polyamide-imide (PAI), polyarylsufone (PAS), polyetherimide (PEI), polyethersulfone (PES), polyphenylene sulfide (PPS) and liquid crystal polymer (LCP), withstand high temperatures, do not degrade when exposed to moisture, and provide exceptional impact resistance and vibrational damping. These characteristics make them useful for items subjected to the relatively high temperatures found in heating ducts.

Referring now to FIGS. 3, 4, 5 and 6, the new micro fragrance dispenser 100 is seen from various angles. The various features of the device are numbered consistent with FIGS. 1 and 2.

Figure 7:
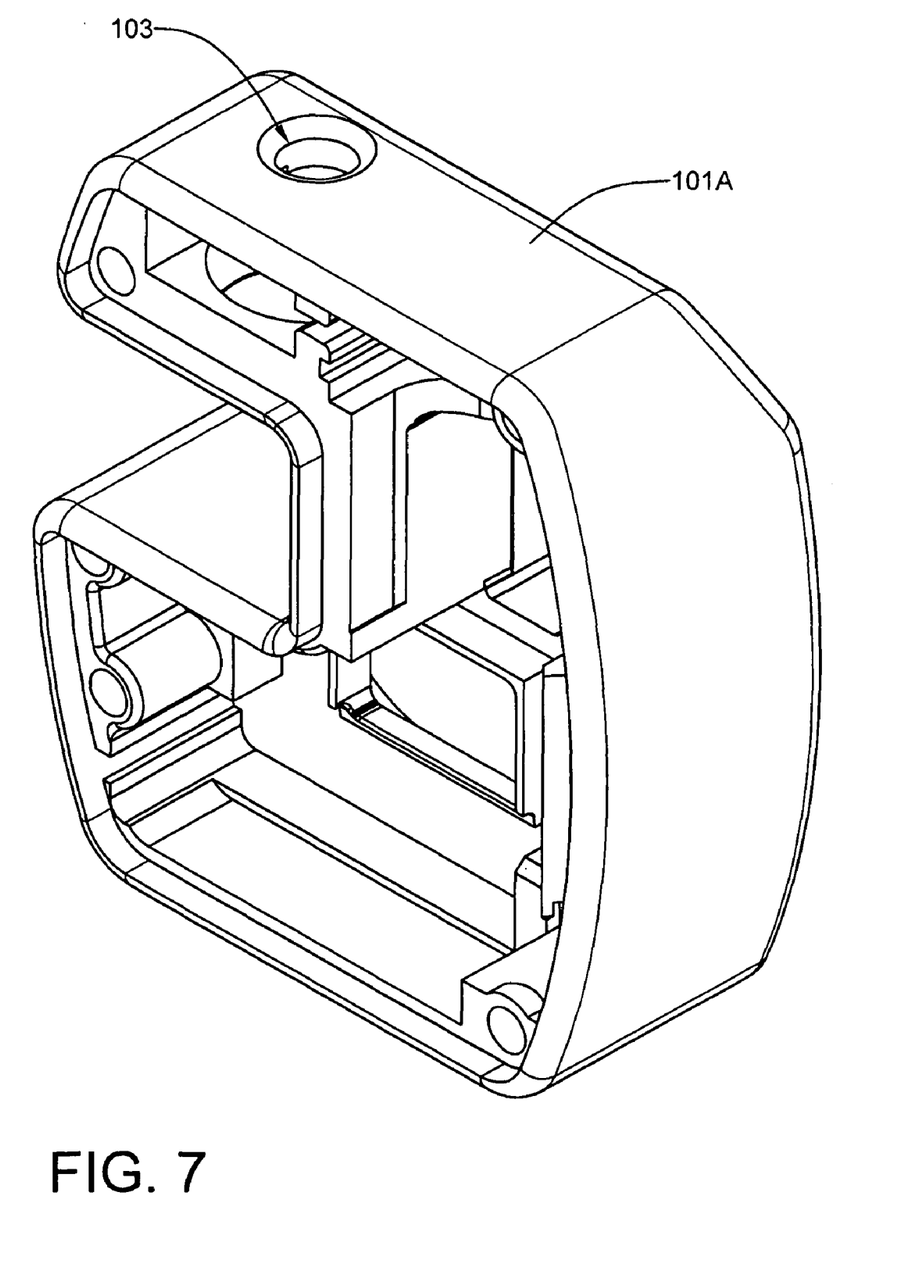
FIG. 7 is an isometric view of the bare dispenser case with the rear panel removed.
Figure 8:
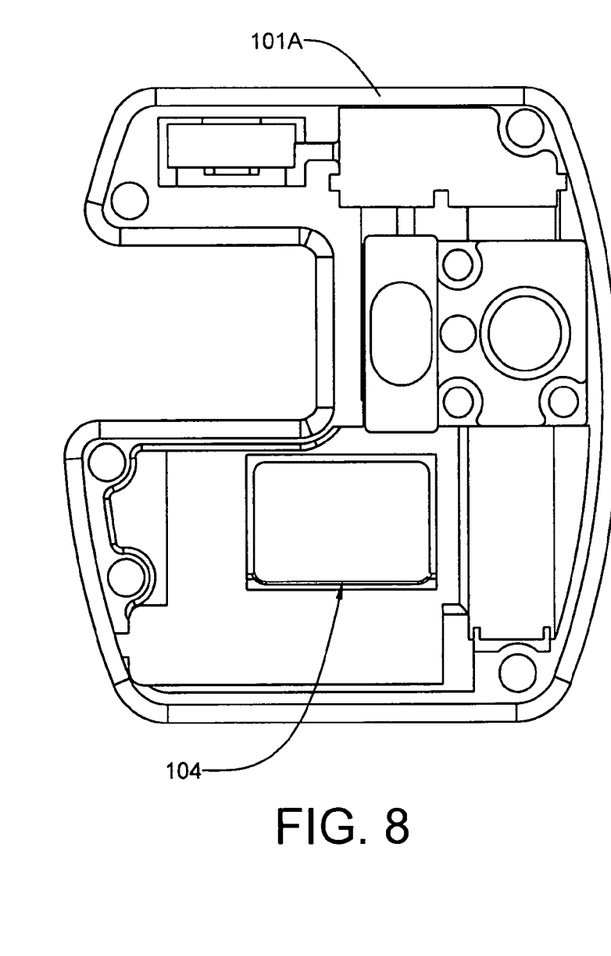
FIG. 8 is a rear elevational view of the bare dispenser case with the rear panel removed.

Referring now to FIGS. 7 and 8, the front main portion 101A of the housing 101 is shown with the rear panel 101B and all internal components removed.

Figure 9:
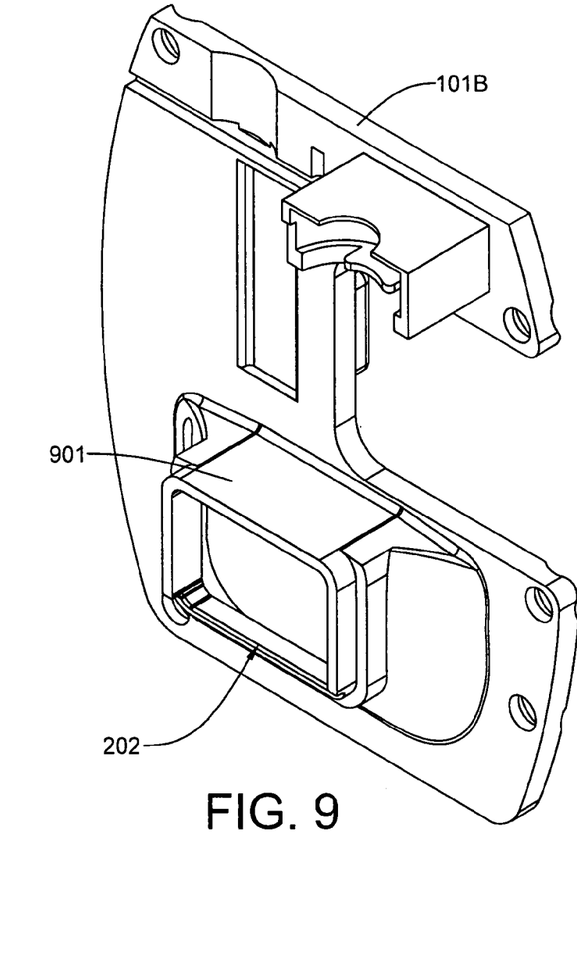
FIG. 9 is an isometric view of the rear panel, showing primarily the inside surfaces thereof.
Figure 10:
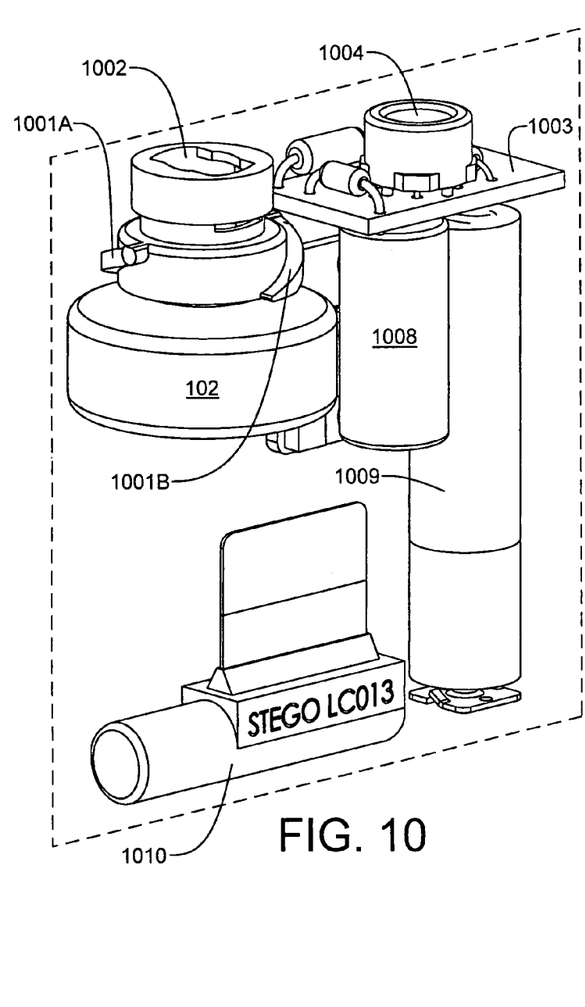
FIG. 10 is an isometric rear view of the internal components of the micro fragrance dispenser, arranged as they would be positioned within the dispenser case.
Figure 11:
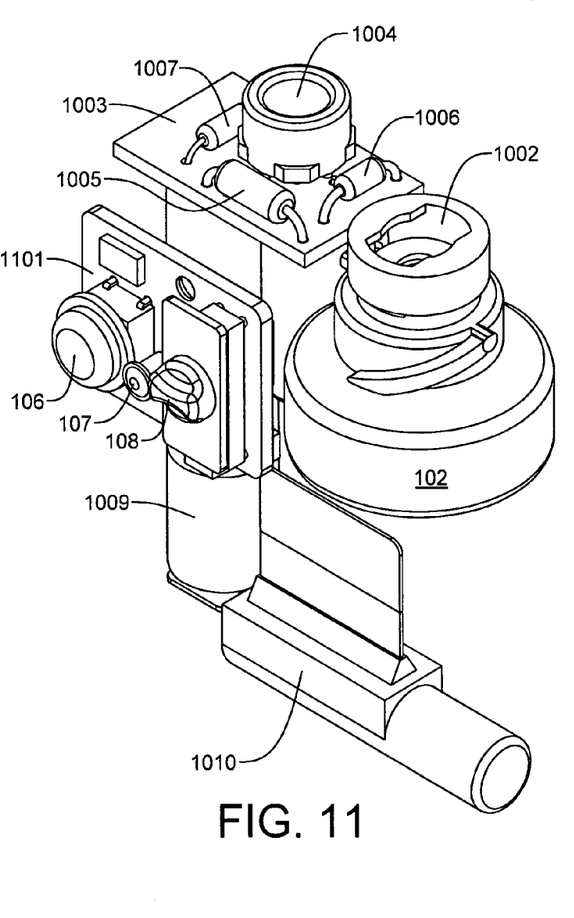
FIG. 11 is an isometric front view of the internal components of the micro fragrance dispenser, arranged as in FIG. 10.
Figure 12:
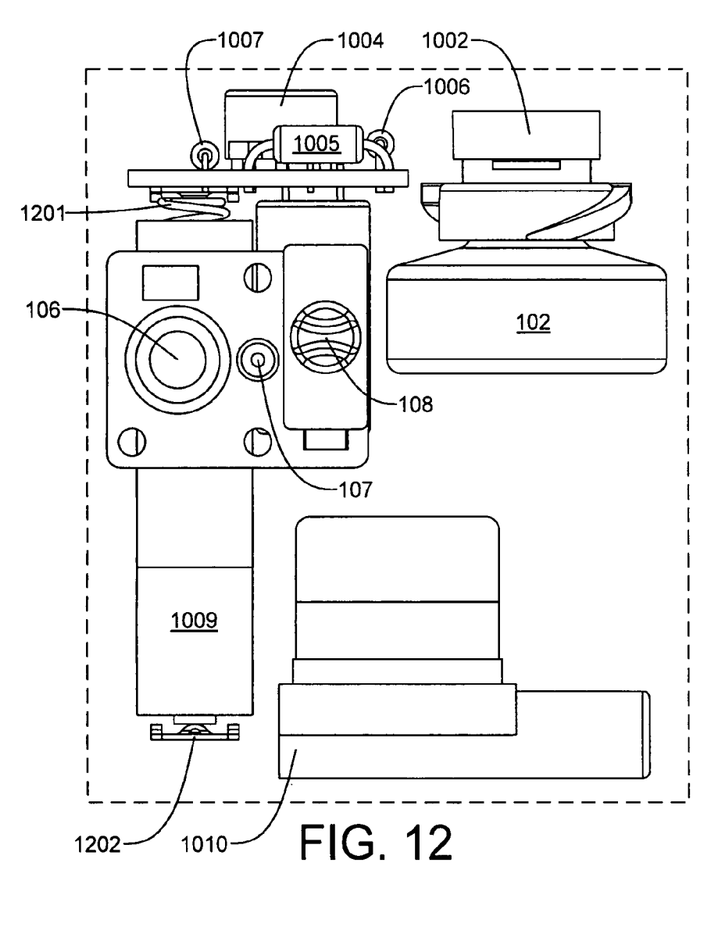
FIG. 12 is a front elevational view of the internal components of the micro fragrance dispenser, arranged as in FIG. 10.
Figure 13:
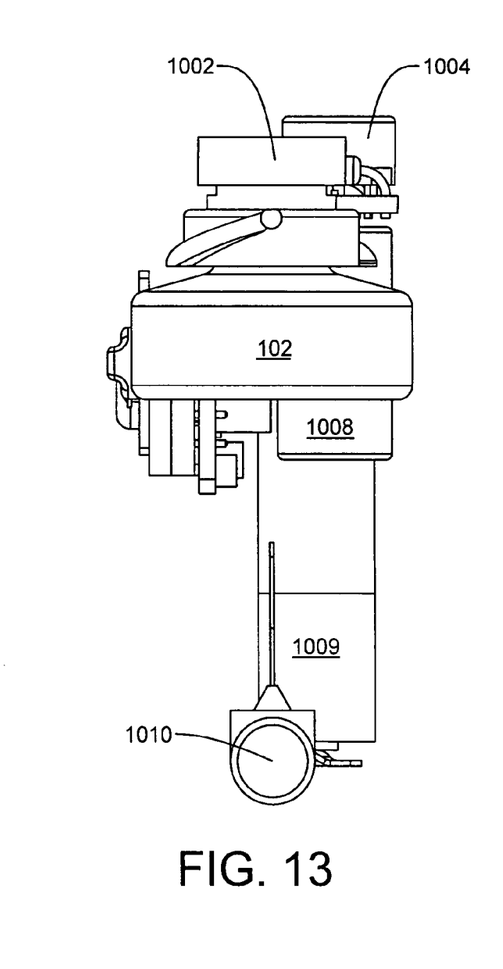
FIG. 13 is right side elevational view of the internal components of the micro fragrance dispenser, arranged as in FIG. 10.
Figure 14:
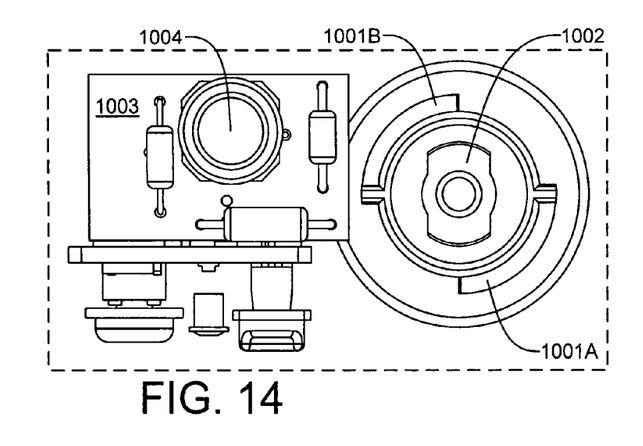
FIG. 14 is a top plan view of the internal components of the micro fragrance dispenser, arranged as in FIG. 10.
Figure 15:
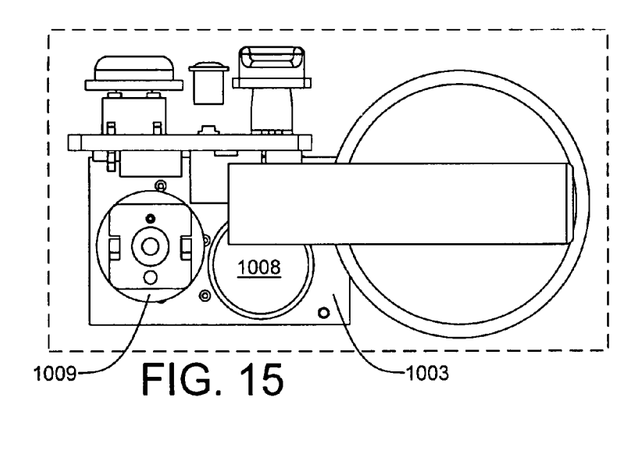
FIG. 15 is a bottom plan view of the internal components of the micro fragrance dispenser, arranged as in FIG. 10.
Figure 16:
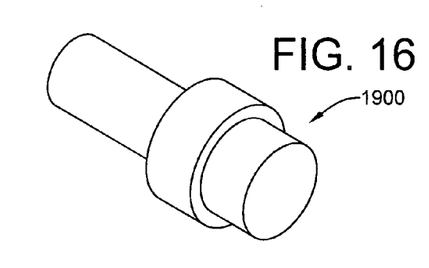
FIG. 16 is an isometric view of the absorbent wick.
Figure 17:
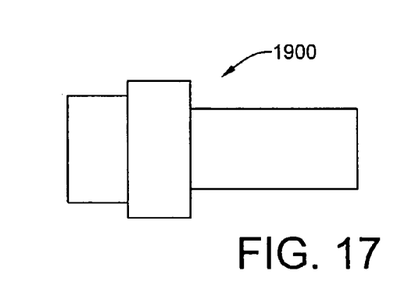
FIG. 17 is a side elevational view of the absorbent wick.
Figure 18:
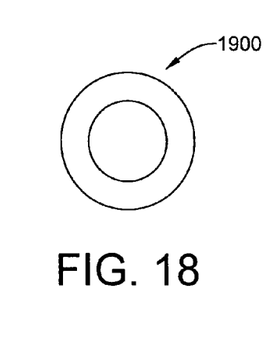
FIG. 18 is a bottom plan view of the absorbent wick.
Figure 19:
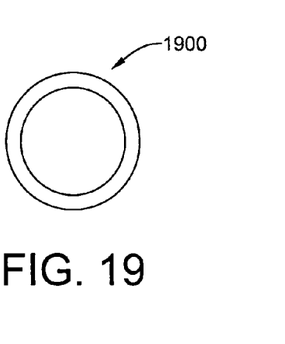
FIG. 19 is a top plan view of the absorbent wick.
Figure 20:
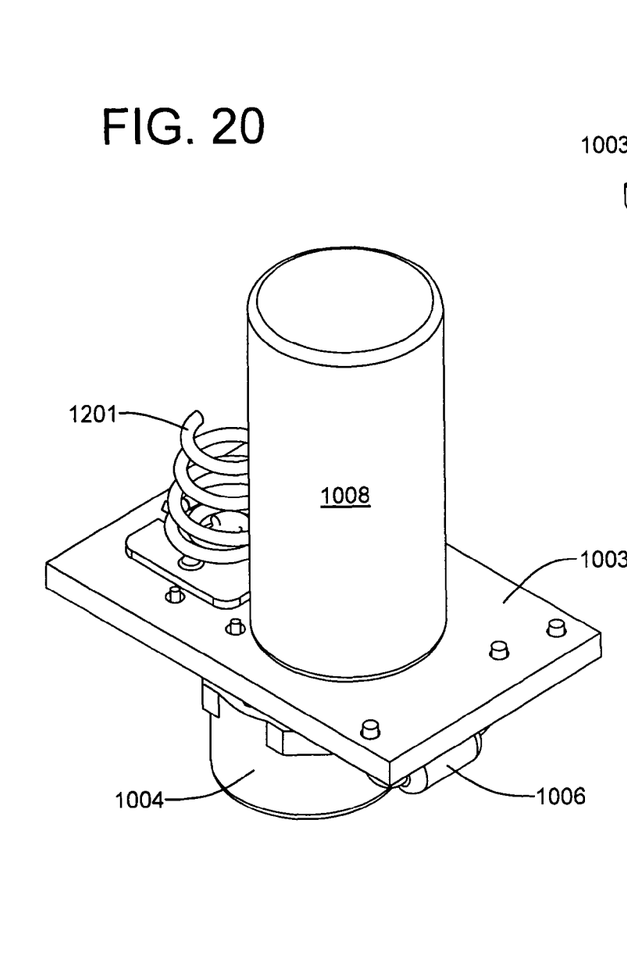
FIG. 20 is an isometric bottom view of a first circuit board assembly on which is mounted a capacitor, a coil, a transistor, a pair of resistors and a resilient battery contact.
Figure 21:
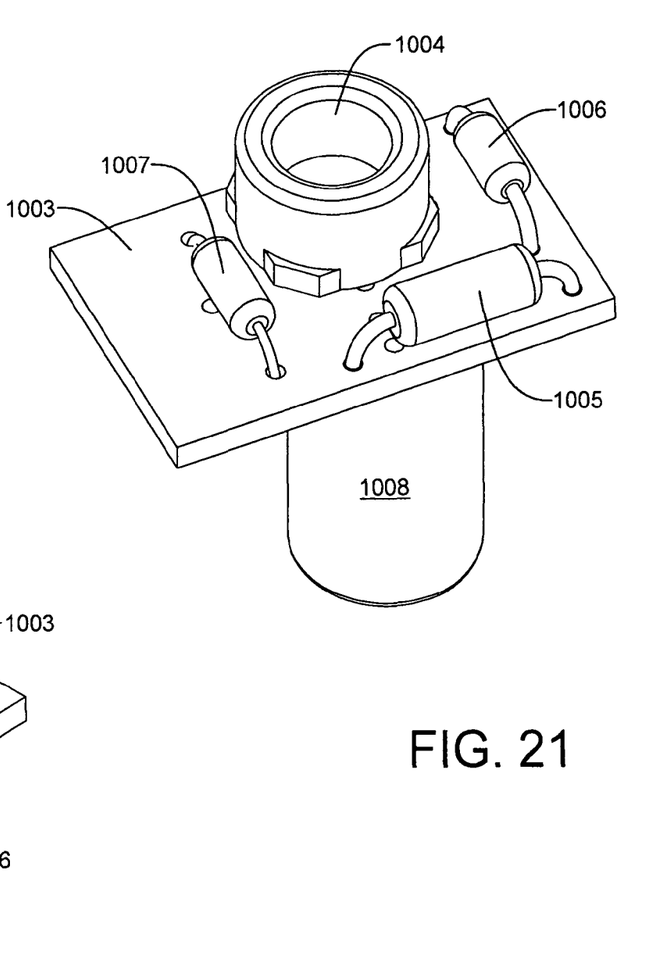
FIG. 21 is an isometric top view of the first circuit board assembly of FIG. 20.
Figure 22:
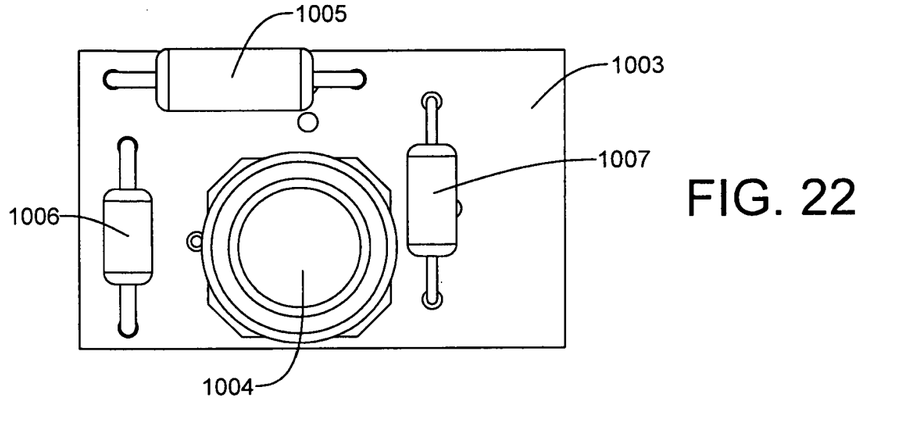
FIG. 22 is a top plan view of the first circuit board assembly of FIG. 20.
Figure 23:
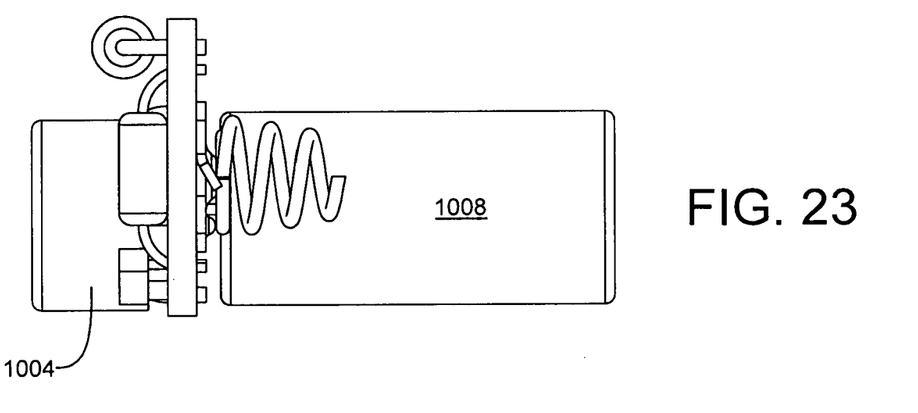
FIG. 23 is a left side elevational view of the first circuit board assembly of FIG. 20.
Figure 24:
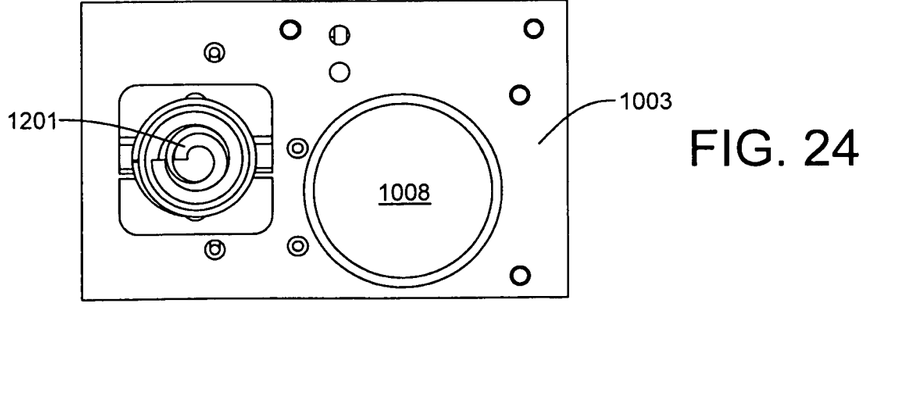
FIG. 24 is a bottom plan view of the first circuit board assembly of FIG. 20.
Figure 25:
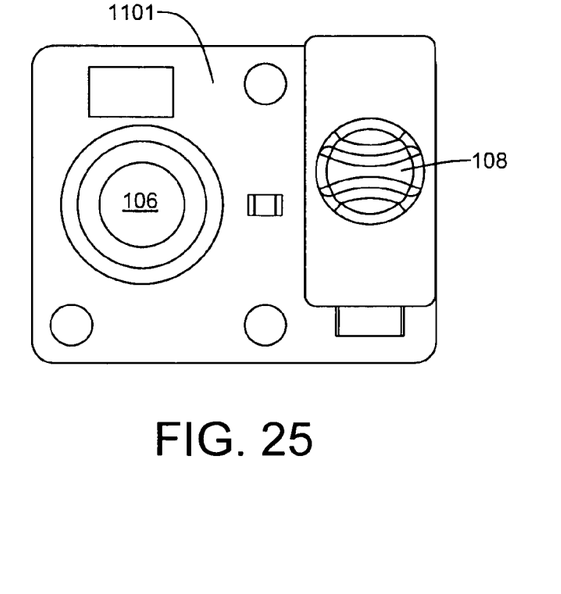
FIG. 25 is a front elevational view of a second circuit board assembly on which is mounted a momentary contact switch and a three-position switch, and a microcontroller.

Referring now to FIG. 9, the shape of the internal surfaces of the rear panel 202 is clearly shown. It will be noted that the rear window 202 has an internal frame 901.

Figure 26:
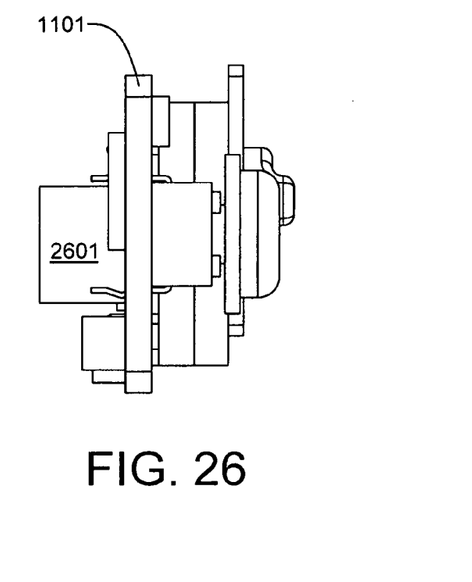
FIG. 26 is a left side elevational view of the second circuit board assembly of FIG. 25.
Figure 27:
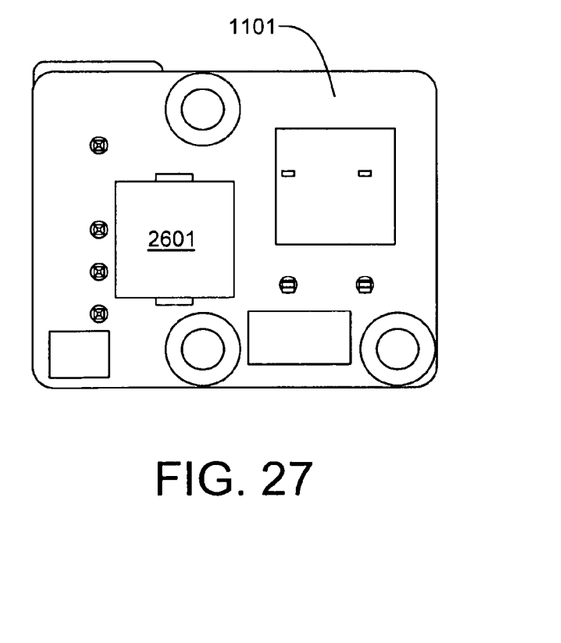
FIG. 27 is a rear elevational view of the second circuit board assembly of FIG. 25.
Figure 28:
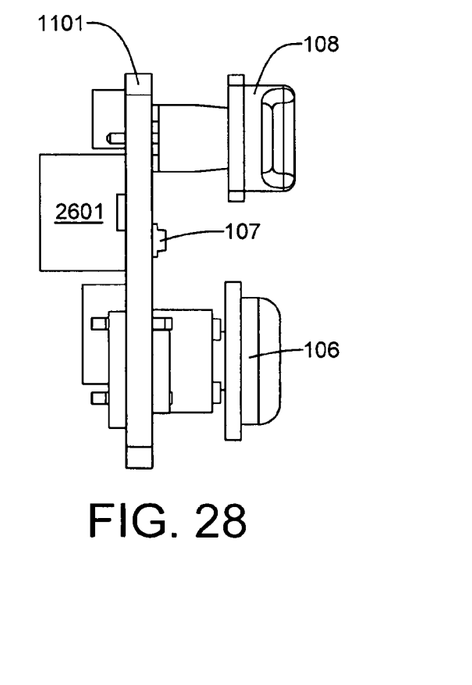
FIG. 28 is a top plan view of the second circuit board assembly of FIG. 25.

Referring now to FIGS. 10 through 15, the internal components of the micro fragrance dispenser 100 are shown arranged as they would be positioned within the dispenser housing 101. In addition, the fragrance-containing reservoir 102 is positioned as it would be when installed within the reservoir receiving socket in the housing 101. It will be noted that the fragrance reservoir 102 incorporates a pair of spiral male threads 1001 that engage a pair of female threads within a socket in the housing 101. Positioned above the fragrance reservoir 102 is a piezoelectric assembly 1002, which emits a fine spray of fragrance oil through the aperture 103 in the top of the housing 101. A first circuit board assembly 1003 has mounted thereon a number of discrete electrical components, including a switching transformer 1004, a transistor 1005, an inductor 1006, a resistor 1007, a capacitor 1008, and a spring-loaded contact 1201 for the negative terminal of a 1.5-volt power cell 1009. A dimpled contact 1202 for the positive terminal of the 1.5-volt power cell 1009 is anchored directly to the housing 101. A Stego LC 013 magnetic reed switch 1010, or equivalent, functions as the air flow detector 105. Originally designed to indicate either proper operation or failure of cooling fans in computer cases, the Stego LC013 provides simple and reliable detection of air is flowing through a heating and air conditioning duct. A second circuit board assembly 1101 has mounted thereon a momentary contact switch 106, a three-position sliding selector switch 108, an indicator LED 107, and a microcontroller 2601 (see FIG. 26). The momentary contact switch 106 temporarily overrides an automatic mode of operation of the micro fragrance dispenser 100 for a set period of time, and will turn on the dispensing of fragrance regardless of air flow. The frequency with which the fragrance is dispensed is set by the three-position sliding selector switch 108. The presently preferred override time is about 15 minutes. After the set period of time has expired, operation reverts to the automatic mode in which fragrance dispensing is effected only when airflow is detected. The three-position sliding selector switch 108 selects a fragrance release rate from three time interval settings: low, medium, and high. The override time, as well as the time interval settings are easily adjustable through reprogramming of the microcontroller 2601. It will be noted that the conductors which interconnect the various components are not shown in the drawings.

Referring now to FIGS. 16 through 19, a wick 1900 is shown that transports the fragrance from the reservoir 102 to the piezoelectric assembly 1002. The wick is made of an absorbent material, such as cotton, linen, rayon, or of synthetic fibers.

Referring now to FIGS. 20 through 24, the first circuit board assembly 1003 is shown separately. The various components on the board are numbered consistent with FIGS. 10 through 15.

Referring now to FIGS. 25 through 28, the second circuit board assembly 1101 is shown separately. The various components on the board are numbered consistent with FIGS. 10 through 15.

As very little processing power is required of the microcontroller 2601, it is preferably one having low cost and low power consumption characteristics. For a presently preferred embodiment of the invention, the microcontroller 2601 is an MC9S08QG8 microcontroller unit (MCU), which is a member of the family of 8-bit microcontroller MCUs based on the HCS08 core, which are manufactured by Freescale Semiconductor, Inc. Of Austin, Tex. Power for all internal electrical components of the micro fragrance dispenser are provided by the 1.5-volt power cell 1009. The power cell 1009 continuously charges the capacitor 1008. When the microcontroller 2601 receives a signal from the airflow detector 105 indicating that air is flowing around the micro fragrance dispenser 100, or the microcontroller 2601 receives a signal generated by depression of the momentary contact switch 106, the microcontroller 2601 switches transistor 1005 on and off at intervals determined by microcontroller programming corresponding to either the particular setting of three-position slider switch 108 or the override condition established by depression of the momentary contact switch 106. Low-voltage DC pulses escape from the capacitor 1008 through the transistor 1005. The low-voltage pulses are transformed to high-voltage pulses by the switching transformer escapes A series of low-voltage current pulses, powered by the 1.5-volt power cell 1009, are output from the transistor 1005. These pulses are sent to the switching transformer 1004, which converts the low-voltage pulses to high-voltage pulses capable of activating the piezoelectric assembly 1002. Voltages in the range of 46 to 98 volts are typically required to activate a piezoelectric device. Each time the piezoelectric assembly 1002 receives a high-voltage pulse, it sprays a small amount of fragrance which has been transported to it from the reservoir 102 by the wick 1900. The pulses continue until either the override period expires or the airflow around the micro fragrance dispenser ceases.

Figure 29:
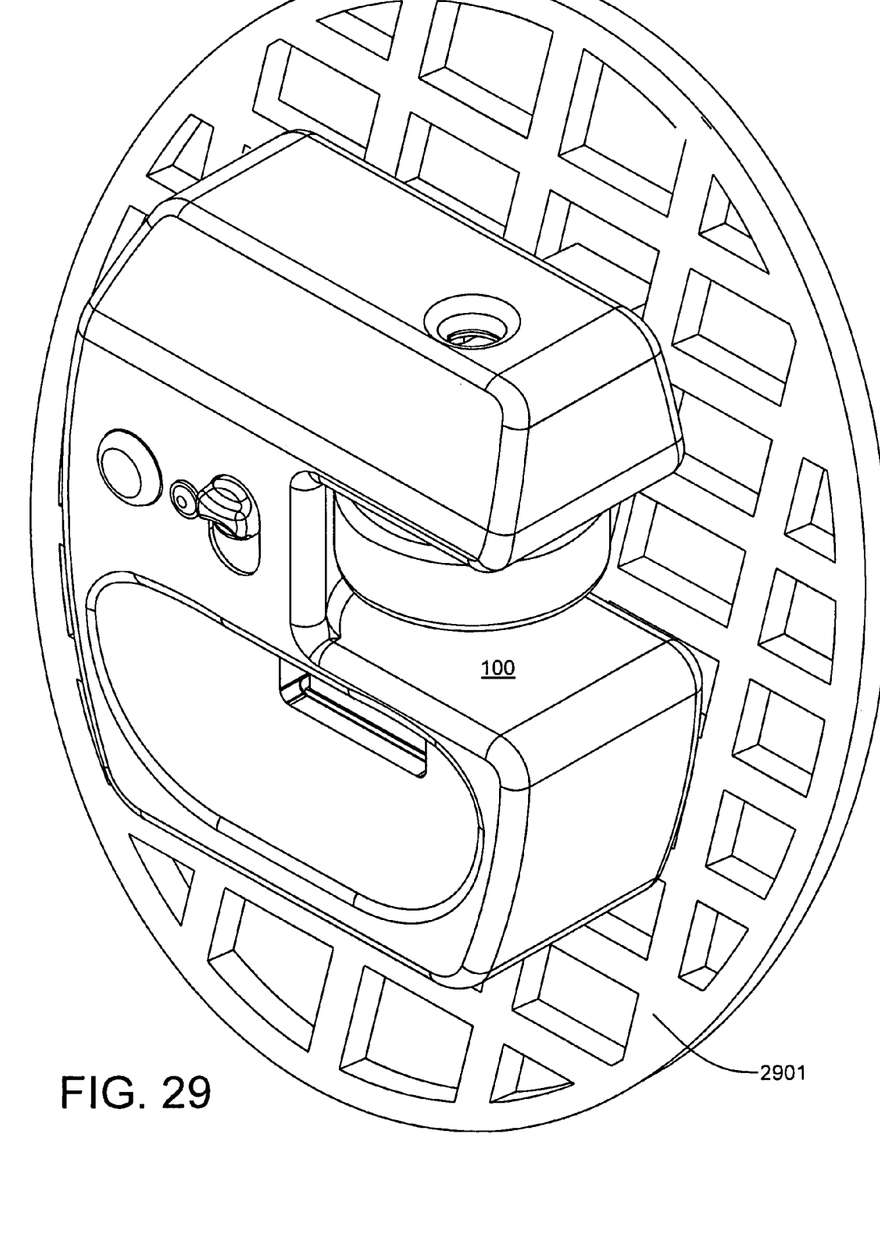
FIG. 29 is an isometric view of the micro fragrance dispenser attached to a heating/air conditioning duct outlet grill of a vehicle.

Referring now to FIG. 29, the micro fragrance dispenser has been attached to the grill 2901 of a heating and air conditioning duct outlet of a vehicle (not shown). The airflow detector 105 monitors air flows from the duct outlet and sends a signal to the microcontroller 2601 whenever it detects the flow of air through the grill 2901.

Although only several embodiments of the fragrance dispenser have been heretofore described, it will be obvious to those having ordinary skill in the art that changes and modifications may be made thereto without departing from the scope and the spirit of the invention as hereinafter claimed.

What is claimed is:

1. A timed aerosol fragrance dispenser for dispensing fragrance into air flow emanating from a heating and air conditioning vent register, the fragrance dispenser comprising:
    a fragrance-containing reservoir;
    a case containing a microcontroller, a magnetic reed switch having a flapper actuator which detects air flow from the vent register, a piezoelectric assembly coupleable to the reservoir for spraying fragrance from the reservoir in timed bursts, a DC power source and circuitry for converting current from the DC power source to pulses having voltage levels sufficient to activate the piezoelectric assembly.

2. The timed aerosol fragrance dispenser of claim 1, wherein said circuitry comprises:
    a capacitor for storing charge from the DC power source;
    a transistor activated by a pulse train generated by the microcontroller;
    a switching transformer coupled to the capacitor through the transistor, the output of said switching transformer being coupled to the piezoelectric assembly.

3. The timed aerosol fragrance dispenser of claim 1, wherein intervals between pulses in the pulse train are switch selectable.

4. The timed aerosol fragrance dispenser of claim 2, wherein the pulse train from the microcontroller is normally generated only when the magnetic reed switch signals to the microcontroller that air flow is emanating from the vent register.

5. The timed aerosol fragrance dispenser of claim 4, wherein the normal programming can be overridden for a set period of time by depressing a momentary contact switch so that a pulse train will be sent to the transistor even in the absence of air flow from the vent register.

6. The timed aerosol fragrance dispenser of claim 1, wherein said magnetic reed switch having a flapper actuator is mounted within a window that penetrates the case.

\* \* \* \* \*